US012702398B2

(12) United States Patent
Krause et al.

(10) Patent No.: US 12,702,398 B2
(45) Date of Patent: Aug. 11, 2026

(54) INDEPENDENT ROD SUSPENSION

(71) Applicant: Stryker European Operations Holdings LLC, Kalamazoo, MI (US)

(72) Inventors: Steven F. Krause, Oakland, NJ (US); Abram Reitblat, Monroe, NY (US)

(73) Assignee: VB Spine US Opco LLC, Leesburg, VA (US)

( * ) Notice: Subject to any disclaimer, the term of this patent is extended or adjusted under 35 U.S.C. 154(b) by 925 days.

(21) Appl. No.: 17/974,865

(22) Filed: Oct. 27, 2022

(65) Prior Publication Data

US 2023/0046932 A1 Feb. 16, 2023

Related U.S. Application Data

(63) Continuation of application No. 16/639,362, filed as application No. PCT/US2018/000326 on Aug. 17, 2018, now Pat. No. 11,523,809.

(60) Provisional application No. 62/546,841, filed on Aug. 17, 2017.

(51) Int. Cl.
*A61B 17/02* (2006.01)

(52) U.S. Cl.
CPC .. *A61B 17/0206* (2013.01); *A61B 2017/0287* (2013.01)

(58) Field of Classification Search
CPC ... A61B 17/02; A61B 17/025; A61B 17/0206; A61B 17/0287; A61B 17/0293
See application file for complete search history.

(56) References Cited

U.S. PATENT DOCUMENTS 3,522,799 A 8/1970 Gauthier
3,749,088 A 7/1973 Kohlmann
3,965,890 A * 6/1976 Gauthier ............ A61B 17/0293 600/233
4,010,741 A 3/1977 Gauthier
4,616,635 A * 10/1986 Caspar .................. A61B 17/02 600/215
5,928,139 A * 7/1999 Koros ................ A61B 17/0206 600/245
6,036,641 A * 3/2000 Taylor ................ A61B 17/0206 600/234

(Continued)

FOREIGN PATENT DOCUMENTS

EP 3443912 A1 2/2019
WO 2012040206 A1 3/2012

(Continued)

OTHER PUBLICATIONS

International Search Report and Written Opinion for PCT/US2018/000326, mailed Nov. 30, 2018.

*Primary Examiner* — Eduardo C Robert
*Assistant Examiner* — Michelle C Green
(74) *Attorney, Agent, or Firm* — Lerner David LLP

(57) ABSTRACT

In one embodiment, an assembly includes a retractor and at least one cylindrical rod attached to the retractor. The rod has a fixed length portion and a spring portion. The spring portion of the rod has a longitudinal dimension that changes as a function of loading on the rod. When the rod is in contact with a solid surface such as a bone, it maintains contact with such surface even while changing shape due to loading on the rod. When the assembly includes multiple rods attached to the retractor, both spring-based rods and other types of rods may be used in combination.

20 Claims, 9 Drawing Sheets

(56) References Cited

U.S. PATENT DOCUMENTS

| | | | | |
|---|---|---|---|---|
| 7,758,501 | B2 | 7/2010 | Frasier et al. | |
| 8,992,558 | B2 | 3/2015 | Stone et al. | |
| 2004/0236316 | A1 | 11/2004 | Danitz et al. | |
| 2005/0137461 | A1 * | 6/2005 | Marchek | A61B 17/025 600/220 |
| 2007/0238265 | A1 | 10/2007 | Kurashina et al. | |
| 2008/0108878 | A1 | 5/2008 | Goodman et al. | |
| 2008/0234551 | A1 | 9/2008 | Lin et al. | |
| 2009/0198240 | A1 | 8/2009 | Kaufman | |
| 2010/0222644 | A1 | 9/2010 | Sebastian et al. | |
| 2011/0295075 | A1 | 12/2011 | Picha et al. | |
| 2013/0237766 | A1 | 9/2013 | Pell et al. | |
| 2014/0330086 | A1 * | 11/2014 | Mire | A61B 17/02 600/215 |
| 2016/0192922 | A1 | 7/2016 | Friedrich et al. | |
| 2017/0007228 | A1 | 1/2017 | Costabile | |
| 2019/0015089 | A1 * | 1/2019 | Rosenbaum | A61B 17/0206 |
| 2019/0053826 | A1 | 2/2019 | Bush, Jr. et al. | |

FOREIGN PATENT DOCUMENTS

| | | | |
|---|---|---|---|
| WO | 2018039228 | A1 | 3/2018 |
| WO | 2019036039 | A2 | 2/2019 |
| WO | 2019036048 | A2 | 2/2019 |

* cited by examiner 102
110
20
108
104
14
12
12

102
110
20
108
104
12
14
12

102
30
104
12
110
20
106
12
14
10

102
12
110
20
108
104
12
14

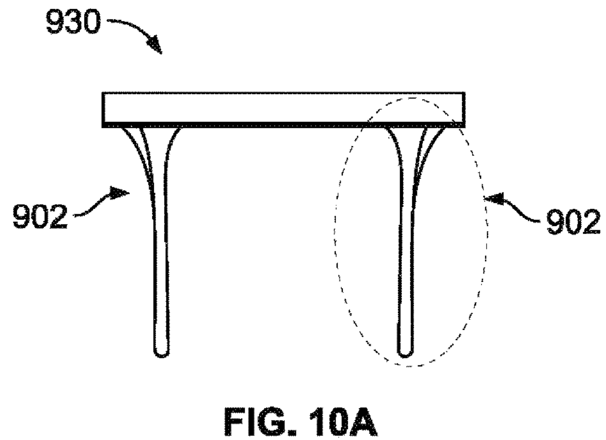
FIG. 10A
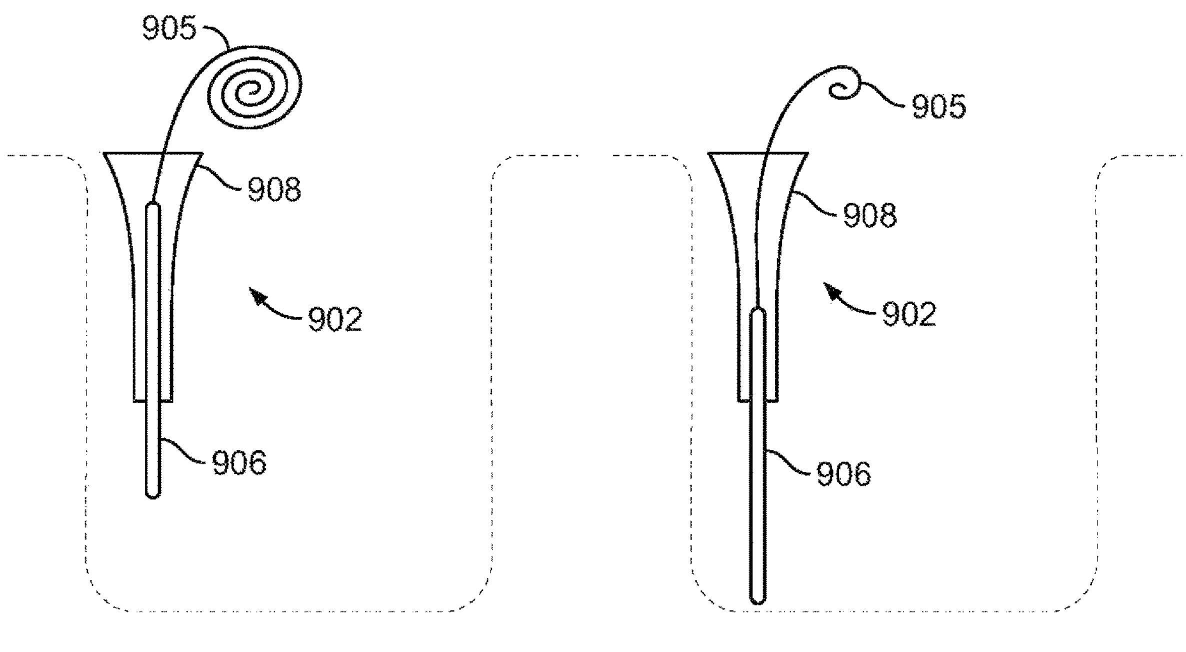
FIG. 10B
FIG. 10C

INDEPENDENT ROD SUSPENSION

CROSS-REFERENCE TO RELATED APPLICATIONS

The present application is a continuation of U.S. patent application Ser. No. 16/639,362, filed Feb. 14, 2020, which is a national phase entry under 35 U.S.C. § 371 of International Application No. PCT/US2018/000326, filed Aug. 17, 2018, published in English, which claims the benefit of the filing date of U.S. Provisional Patent Application No. 62/546,841, filed on Aug. 17, 2017, the disclosures of which are hereby incorporated by reference herein in their entirety. Additionally, the disclosures of commonly owned WO2018/039228, filed Aug. 22, 2017 (the '228 Publication), and commonly owned U.S. Provisional Patent Application Nos. 62/546,780 ("the '780 Application"), 62/546,847 ("the '847 Application"), 62/546,796 ("the '796 Application) and 62/650,579 ("the '579 Application), are also hereby incorporated by reference herein in their entirety.

BACKGROUND OF THE INVENTION

Spinal implants are commonly utilized in spinal procedures designed to treat spinal maladies. Such implants are used, for example, to immobilize and fuse adjacent vertebral bodies. This often plays a critical role in addressing spinal diseases or injury, or otherwise treating pain in a patient.

Various techniques have been developed and are often employed to access the spine during a spinal implant implantation procedure. These techniques are often dictated by the type of implant being utilized. For example, the spine may be accessed using a posterior approach, an anterior approach, or a lateral approach. Among these, a lateral approach is advantageous in that a portal to access a surgical site may be larger than with other approaches, thus allowing for a larger implant to be used, which experience over time has shown tends to improve the overall outcome of the procedure.

One method for implanting lateral implants is via a lateral trans-psoas approach. This typically involves the creation of an incision on the lateral side of the patient. Thereafter, a path to a surgical site, i.e., the vertebral bodies, is systematically created. One technique to accomplish this involves the use of sequential dilators, where an insertion of each dilator over another progressively increases the size of a tissue area displaced by the dilators. Once the dilators have displaced a sufficient amount of tissue for the procedure, a retractor, ring or other stabilizing structure is used to preserve an opening. Retractors typically include a plurality of blades that are designed to rest against the vertebral bodies and hold the tissue open to allow access for the surgeon. In a variant, a narrow retractor employing blades in the form of rods is initially inserted and sequential dilation is used to move the rods apart and create the path to the surgical site.

One challenge with existing access systems relates to the rigidity and lack of responsiveness of structural elements left in place to define a surgical path during the procedure. Many spinal procedures require hammering and other high impact contact at the surgical site, causing the spine to deflect and in some cases make contact with the blades or rods as it returns from its deflected shape. This may damage the spine or may cause blades or rods to shift from their intended position in the portal. Moreover, if the blades or rods have shifted away from the spine, the risk of tissue creep into the surgical path increases. To prevent these adverse outcomes, the position of the blades or rods must be manually adjusted, which slows down surgery.

Thus, there is a need for improved structures and methods used to preserve a path to a surgical site during surgical procedures.

BRIEF SUMMARY OF THE INVENTION

In one aspect, the present disclosure relates to an assembly. In one embodiment, the assembly includes a retractor and at least one rod attached to the retractor. The at least one rod includes a fixed length portion and a spring portion and is structured so that a portion of the rod is configured to be in contact with a surface of a bone.

In one embodiment, the spring portion absorbs at least some of a first load applied to the at least one rod when the at least one rod is in contact with a surface. In a variant, the spring portion changes in length in response to the first load applied to the at least one rod when the at least one rod is in contact with the surface. In another embodiment, the spring portion of the at least one rod includes a length adapted to vary in its alignment relative to the fixed length portion such that the length is movable between positions linear and non-linear with the fixed length portion. In a variant, the spring portion is positioned at a leading end of the at least one rod. In yet another embodiment, the fixed length portion includes an opening therein and the spring portion is at least partially disposed within the opening.

In one embodiment, the at least one rod also includes a central rod and a second fixed length portion. The central rod extends from the fixed length portion while the second fixed length portion includes an opening so that the central rod may be partially disposed in the opening. Disposal of the central rod in the second fixed length portion is from an end of the central rod remote from the fixed length portion. In this embodiment, the spring portion is disposed over the central rod such that the spring portion extends between the fixed length portion and the second fixed length portion.

In one embodiment, the spring portion is remote from an insertion end of the at least one rod and the insertion end configured to make contact with the surface of the bone. In a variant, the at least one rod also includes a central rod structured for disposal in an opening of the fixed length portion so that a portion of the central rod outside of the fixed length portion is surrounded by the spring portion. The fixed length portion is configured to make contact with the surface when the at least one rod is in contact with the surface.

In another embodiment, the fixed length portion of the at least one rod includes an opening therethrough for disposal of a central rod therein and the spring portion is configured for attachment outside of and around both the fixed length portion and the central rod. In yet another embodiment, the spring portion of the at least one rod is a wound coil and at least part of the spring portion is disposed within the fixed length portion such that the at least one rod increases in length as the wound coil is unwound. In a variant, the at least one rod also includes a second fixed length portion extending from an end of the spring portion disposed within the fixed length portion.

In another aspect, the present disclosure relates to a retraction system configured to create openings in tissue of a patient. The retraction system includes a first rod and a second rod. The first rod includes an insertion end, a trailing end, and a portion that absorbs load from a surface when in contact with the surface. The second rod includes an insertion end and a trailing end. The first rod has a length that varies in that it has a first length when the insertion end is not in contact with a surface and a second length when in contact with a surface, the second length being shorter than the first length.

In one embodiment, the first rod, when in contact with a curved surface, is configured to maintain contact with the curved surface such that an end face of the first rod is flush with the curved surface and a portion of a length of the first rod is curved. In another embodiment, the retraction system also includes an adjustment structure secured to a fixed location at one end and a retractor frame holding the first and second rods at a second end, the adjustment structure configured so that first and second rods are movable relative to the fixed location. In a variant, the adjustment structure includes a member with a spring.

In one embodiment, the first rod includes an external shaft, an inner shaft and a spring, the spring and a portion of the inner shaft disposed within a cavity in the external shaft. In a variant, the spring extends from an end of the cavity closest to the trailing end of the first rod to an end of the inner shaft closest to the trailing end of the first rod. In another variant, the portion of the inner shaft disposed in the cavity is disposed in the cavity when the spring is at maximum compression and at maximum extension.

In another aspect, the present disclosure relates to a method involving the use of a retractor with a plurality of rods. In one embodiment, the method involves the following steps: positioning a retractor apparatus with a plurality of rods secured thereto over a surgical site so that the rods are in alignment with the surgical site, and, advancing the plurality of rods from outside of a body of a patient, through the body until at least one of the plurality of rods contacts a bone surface. During the advancement step, the at least one rod that contacts the surface compresses in response to resistance from the hard tissue.

In one embodiment, the method includes a step of contacting the surface such that the hard tissue surface moves relative to the retractor apparatus, the at least one rod maintaining contact with the hard tissue surface when the hard tissue moves relative to the retractor apparatus. In a variant, the hard tissue surface is curved where the at least one rod contacts the hard tissue surface, and a portion of a length of the at least one rod curves to maintain contact with the hard tissue surface.

In another embodiment, the at least one rod also includes a spring portion and the compression in the at least one rod occurs in the spring portion. In a variant, the at least one rod includes an external shaft and an inner shaft and the external shaft axially translates in concert with the compression of the spring portion. In another variant, the spring portion is between an upper fixed length portion and a lower fixed length portion of the at least one rod such that the compression of the rod only occurs remote from the tailing and insertion ends of the rod. In yet another variant, the at least one rod includes an external shaft and an internal shaft, the internal shaft being partially disposed within the spring portion and axially translating in concert with the axial translation associated with the compression of the spring portion.

In yet another embodiment, the at least one rod includes a coiled spring, an external shaft and an internal shaft, the coiled spring partially disposed in a cavity of the external shaft and connected to the internal shaft. In this embodiment the compression of the at least one rod is based on a withdrawal of the coiled shaft from the cavity. In yet another embodiment, the method includes a step of adjusting a depth of one of the plurality of rods independent of at least one other of the plurality of rods.

BRIEF DESCRIPTION OF THE DRAWINGS

A more complete appreciation of the subject matter of the present disclosure and the various advantages thereof can be realized by reference to the following detailed description, in which reference is made to the following accompanying drawings:

FIG. 10A is a side view of a retractor assembly with an adjustable rod structure secured thereto according to one embodiment of the present disclosure.

FIG. 10B is a cross-sectional view of a single adjustable rod of the adjustable rod structure of FIG. 10A in a withdrawn configuration.

FIG. 10C is a cross-sectional view of the single adjustable rod of FIG. 10B in an extended configuration.

DETAILED DESCRIPTION

When referring to the specific directions in the following discussion of certain surgical instruments, methods, and systems, it should be understood that such directions are described with regard to the surgical instruments orientation and position during exemplary application in the human body. Thus, as used herein, the term "proximal" means close to the heart, and the term "distal" means more distant from the heart. The term "anterior" means toward the front of the body or the face, and the term "posterior" means toward the back of the body. The term "medial" means toward the midline of the body, and the term "lateral" means away from the midline of the body.

The present disclosure will largely be discussed in connection with retractors having rods, like the retraction mechanisms disclosed in the '228 Publication. However, it should be understood that the present application has applicability to retractors having more traditional blade structures. Indeed, the adjustable concepts employed in the rods shown and discussed in the present application could be applied to bladed structures as well.

Figures 1A, 1B, 1C, 1D:
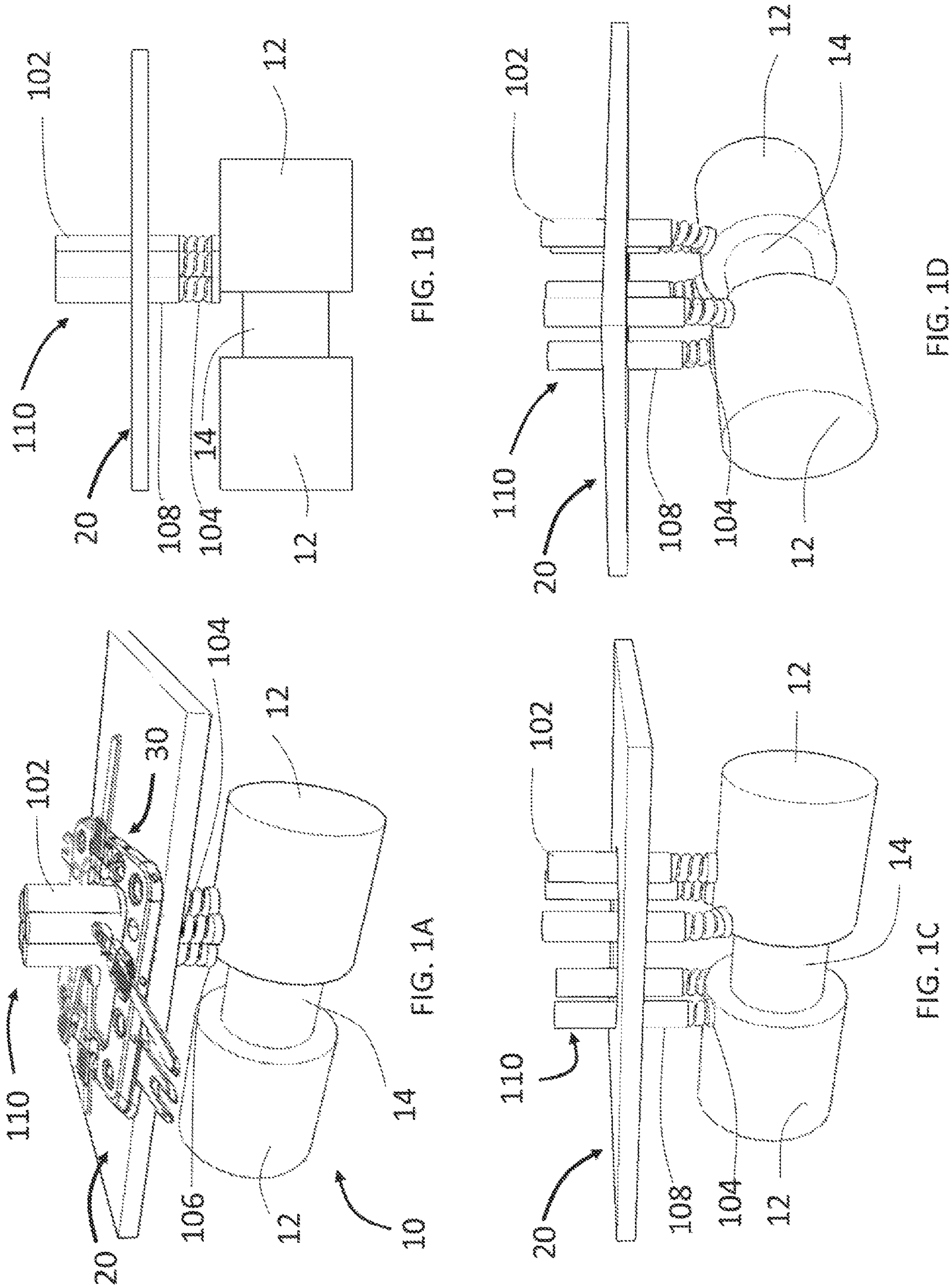
FIG. 1A is a perspective view of an adjustable rod structure advanced to a surgical site in a retracted position and secured to a retractor assembly according to one embodiment of the present disclosure.
FIG. 1B is a side view of the adjustable rod structure of FIG. 1A.
FIG. 1C is a perspective view of the adjustable rod structure of FIG. 1A in a distracted position.
FIG. 1D is another perspective view of the adjustable rod structure of FIG. 1A in a distracted position.

FIG. 1A depicts a retractor system 30 similar to that disclosed in the '228 Publication, with an adjustable support structure 110 having five rods 102 attached thereto. To access a surgical site, a path or portal is created in a body of a patient and the adjustable rod structure is inserted in the retracted or closed position shown in FIGS. 1A and 1B. In one approach, the rods are then moved to a distracted position (best shown in FIGS. 1C and 1D) using sequential dilation, a process whereby a series of elements are inserted one over the other to increase the portal size by displacing tissue 20. One variant of such a process is described in the '847 Application. Of course, other methods may be utilized to distract the rods in accordance with the present disclosure.

Unlike traditional instrumentation employing a series of static blades or rods, adjustable rods 102 include an automatic, spring loaded adjustment mechanism. This allows the rods to follow the spine as the spine moves during a spinal procedure and also allows ends of the rods to conform to curvature and structure of the spine and maintain contact during any surgical procedure. Because the rods maintain contact with the spine, the effects of tissue creep are at a minimum reduced if not substantially negated.

As noted above, adjustable rod structure 110 includes five adjustable rods 102, each with a fixed length portion 108 and a spring portion 104. Fixed length portion 108 extends from a proximal end of adjustable rod 102 and terminates at spring portion 104, which extends to a flat end face 106 at a distal end of adjustable rod 102. As described in greater detail below, a depth of each rod 102 is configured to be independently adjustable relative to other rods when all rods are secured to a retractor.

Fixed length portion 108 is cylindrical in shape and is of a size and material to provide the necessary capacity to retract tissue when bearing laterally thereon. The fixed length portion is engineered to withstand a certain amount of deflection under loading. In this manner, the properties of the rod provide sufficient elastic flexibility to withstand deflection that can result from tissue bearing on the rods during use without reaching yield under the highest possible loads. The maintenance of below yield stresses on the rods ensures that the rods return to their original shape once loads are removed, and thus increases the life cycle of the rods. Flexibility in the rods as described above is determined as a function of the rod length, its cross-sectional area and material properties of the rod. An example of flexible rods is described in U.S. Pat. No. 8,992,558, the disclosure of which is hereby incorporated by reference herein.

Figure 2:
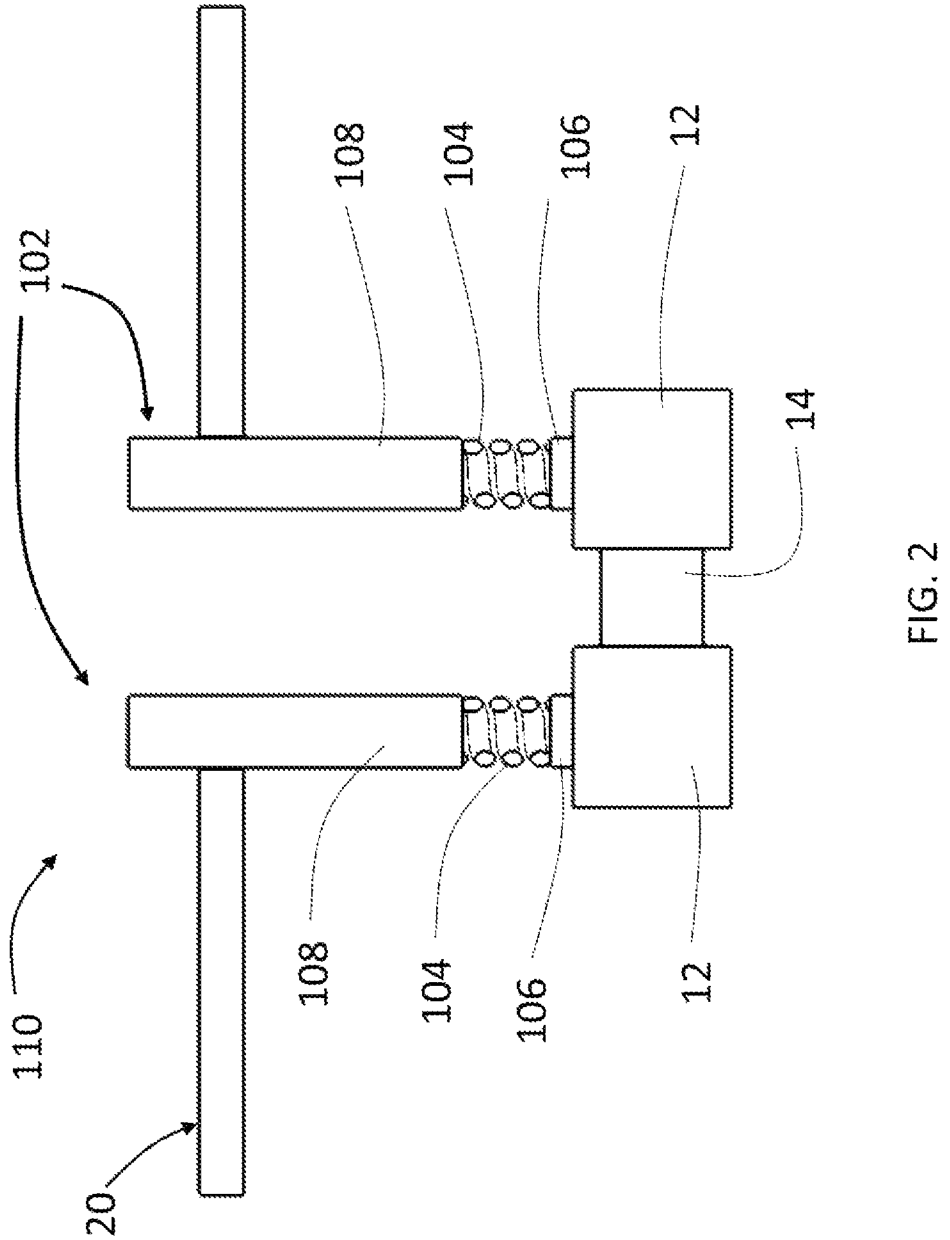
FIG. 2 is a cross-sectional view of the retracted adjustable rod structure of FIG. 1C.

Spring portion 104, as shown in FIG. 2, is configured to vary in length between a compressed and an expanded state. Preferably, such variation in the length of the spring portion is between 5 mm and 10 mm. However, the spring portion can be structured to vary in length to a lesser or greater amount. For example, a spring portion with a greater length variation may be warranted where it is anticipated that a space between a rod fully advanced into the body and a bone surface below it varies relative to other rods of the retractor. In such cases, it is desirable to have springs that can extend a significant amount to reach a bone surface much further away than bone surfaces below other rods. This extra distance can be approximately equal to a radius of a vertebral body below the rod.

Spring portion 104 also provides a capacity to bend in three dimensions. In this manner, a longitudinal axis of spring portion 104 can deviate from a like axis through a length of fixed length portion 108 of the adjustable rod. Such properties allow flat end face 106 to interface with the vertebral bodies 12 even where such vertebral bodies 12 curve or otherwise extend away from the other rods. Put another way, spring portion 104 is structured so that each adjustable rod 102 is conformable to a curved bone surface or other uneven or slanted surface, horizontally and vertically, and on any number of planes in between. Additionally, spring portion 104 is a coiled spring which has an inherent capacity to absorb at least some loads borne by the adjustable rod 102 (e.g., during impaction of a spinal implant). Spring portion 104 is securable to adjustable rod 102 through a press-fit or weld connection; although any other mechanical or chemical securing means is also contemplated, such as the use of fasteners, adhesives, screws or a chemical bond. Similarly, flat end face 106 is secured to spring portion 104 through a like connection. Materials and shape for flat end face 106 are a matter of design choice although one of ordinary skill will appreciate that compatibility with bone surfaces and an environment inside the body are important considerations for the design.

The adjustable rod structure shown in FIGS. 1A-D and 2 may be varied in many ways. For example, the proportion of the overall length of the rod that forms the spring can be greater than that shown in FIG. 2. In other examples, the spring may have a larger or smaller cross section than the fixed length portion. The cross section of either the fixed length portion or the spring portion may be of a non-circular shape such as a rectangular shape and the cross section of each portion may be unique relative to the other. Also, the coil of the spring itself may have a non-circular shape, and may be flat, for example. Other examples employ alternatives to a coil spring including the use of different spring forms, or a rubber, plastic, nylon, or other suitable material component with an appropriate structural configuration for inclusion in a rod construct. An important feature of such a component is its ability to expand, compress and/or bend out of its axis in an elastic fashion when subject to a load so that it returns to its initial shape following the withdrawal of the load. These alternatives are also contemplated for the other embodiments of this disclosure, particularly as alternatives to springs or compressible polymers.

While the embodiment of FIGS. 1A-D and 2 depicts five rods, it is contemplated that adjustable support structure 110 may include any number of rods. Further, it is contemplated that adjustable rods with a spring component may represent less than all of the rods in the adjustable rod structure, and may be used in combination with standard, generally fixed length rods. Similarly, an adjustable rod structure in position within a patient may be modified to have a rod removed and replaced with an adjustable rod as described above. As noted above, the embodiments and examples described herein can be employed with a retractor assembly as shown in FIG. 1A or in other retractor assemblies capable of facilitating the rod retraction process. In other examples, adjustable rod structure may include a fixed length portion and a spring portion alone, without a flat end face element. Again, the adjustable concepts may be employed in more traditional bladed structures as well.

Figures 3, 4:
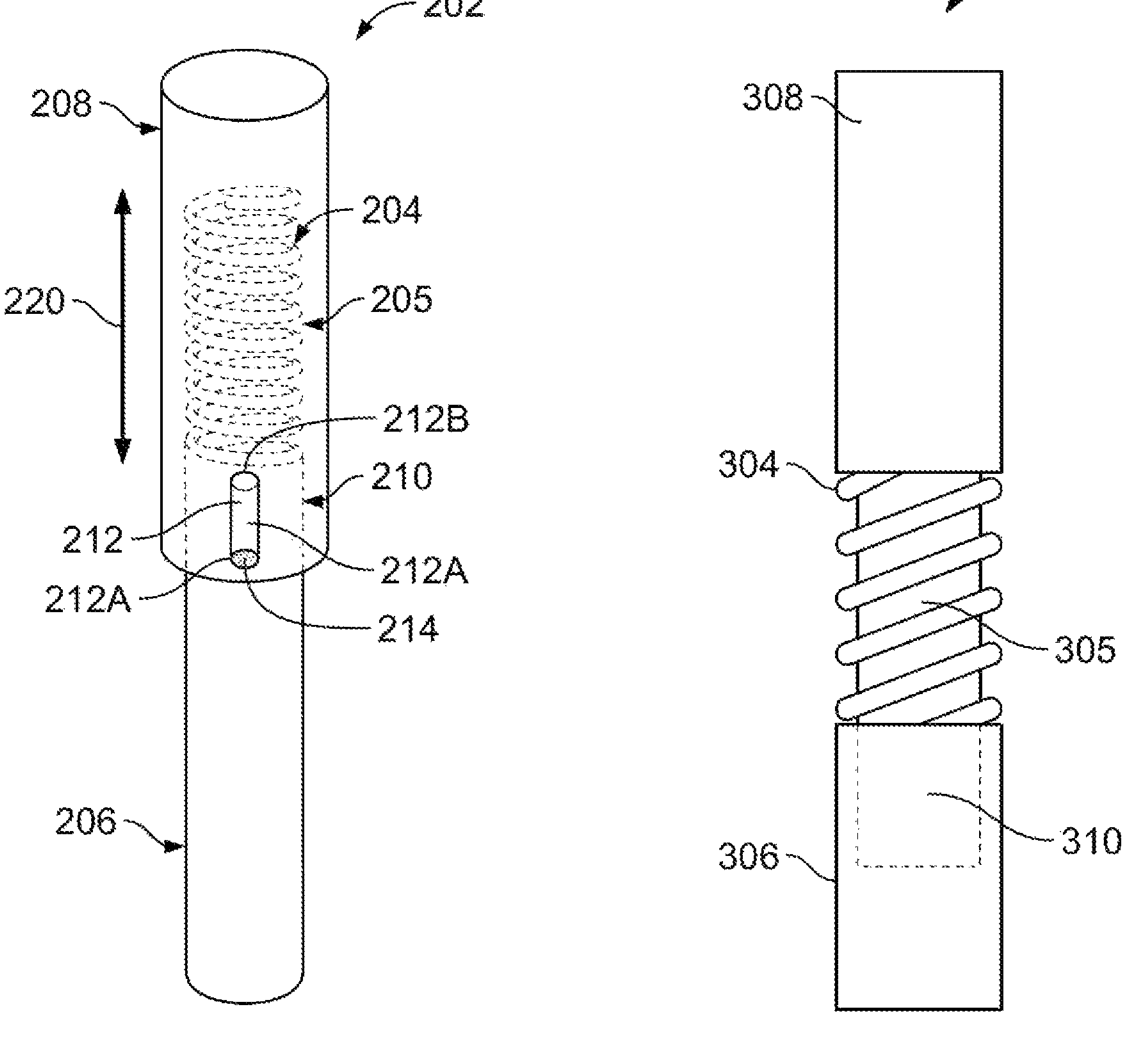
FIG. 3 is a perspective view of an adjustable rod according to another embodiment of the present disclosure.
FIG. 4 is a perspective view of an adjustable rod according to another embodiment of the present disclosure.

In another embodiment shown in FIG. 3, an adjustable rod 202 includes an external shaft 208, an internal shaft 206 and a spring element 204 disposed therebetween. External shaft 208 includes a slot 212 thereon oriented so that it extends in a direction parallel to a length of adjustable rod 202. External shaft 208 is hollow and defines a cavity therein. The cavity within external shaft 208 is sized so that an internal shaft 206 is disposable therein. Internal shaft 206 includes a protrusion in the form of a mechanical stop element 214, which, when adjustable rod 202 is assembled, is positioned within slot 212 so that internal shaft 206 extends into the cavity of external shaft 208. Axial movement of external shaft 208 in the direction of arrow 220 is limited by ends 212A, 212B of slot 212. In this manner, slot 212 prevents spring element 204 from completely ejecting the external shaft from the internal shaft or vice versa.

Spring element 204 extends from an end of internal shaft 206 to an end of the cavity of external shaft 208, as shown in FIG. 3. Spring element 204 and an upper portion 210 of internal shaft 206 abut or are otherwise restrained from lateral movement due to a wall 205 of the external shaft 208 cavity, also shown in FIG. 3.

The adjustable rod shown in FIG. 3 may be varied in many ways. For example, although a mechanical stop is described as operating in conjunction with a slot to control limits on the expansion and contraction of the adjustable rod, other structures achieving such a result as understood by one of ordinary skill in the art are also contemplated. Further, the adjustable rod structure may have an internal and/or external shaft with a tapering diameter, which may improve safety in the process of inserting the rod. Although the adjustable rod is shown with a circular cross-section, other non-circular cross sectional shapes are also contemplated as described, for example, in the above embodiments.

FIG. 4 depicts yet another embodiment of the adjustable rod. Adjustable rod 302 includes an upper portion 308, an inner portion 305, a lower portion 306 and a spring portion 304. Upper portion 308 as shown is generally cylindrical and is abutted by spring portion 304 and inner portion 305. Inner portion 305 is attached to and extends from upper portion 308. Lower portion 306 includes a cavity 310 therein that functions as a guide sized so that inner portion 305 is disposable therein, as best shown in FIG. 4. A distance exists between upper portion 308 and lower portion 306, within which spring portion 304 is disposed, and spring portion 304 surrounds inner portion 305. Cavity 310 is sized and includes a depth so that sufficient room exists for inner portion 305 to translate therewithin, remaining at least partially in the cavity even in the most compressed condition of spring portion 304. In this way, a range of compression and expansion is possible. Spring portion 304 is connected to upper and lower portions 308, 306 through a press-fit or weld connection, or through other means as described above for adjustable rod 102. Securement of spring portion 304 to lower portion 306 ensures adjustable rod 302 maintains integrity in a fully extended state.

As mentioned above, lower portion 306 has a cavity 310 that houses a portion of inner portion 305 beyond the geometry of spring portion 304. The inner portion resides within lower portion 306 while generally not interfacing with walls of cavity 310. However, some contact with walls of the cavity is expected and does not affect the performance of the adjustable rod. An advantage of this embodiment is the unique placement location of the spring. Because spring is located between end members, the adjustable rod operates to have dynamic contact with both a retractor assembly and a surface such as a bone surface. This is because the effects of the spring work in both directions toward the ends of the adjustable rod.

In variants of the above embodiment, the spring may be substituted with other elastic structures as described above. In other variants, the cavity within the lower portion of the adjustable rod may include additional surface features or other mechanical features to limit the extent to which the inner portion is drawn out of the cavity as the spring is extended. Such a configuration could be implemented where the adjustable rod is expected to undergo significant tension and therefore expand in length to a significant degree. In such cases, it may be necessary to control the extent to which the spring can expand.

Figure 5:
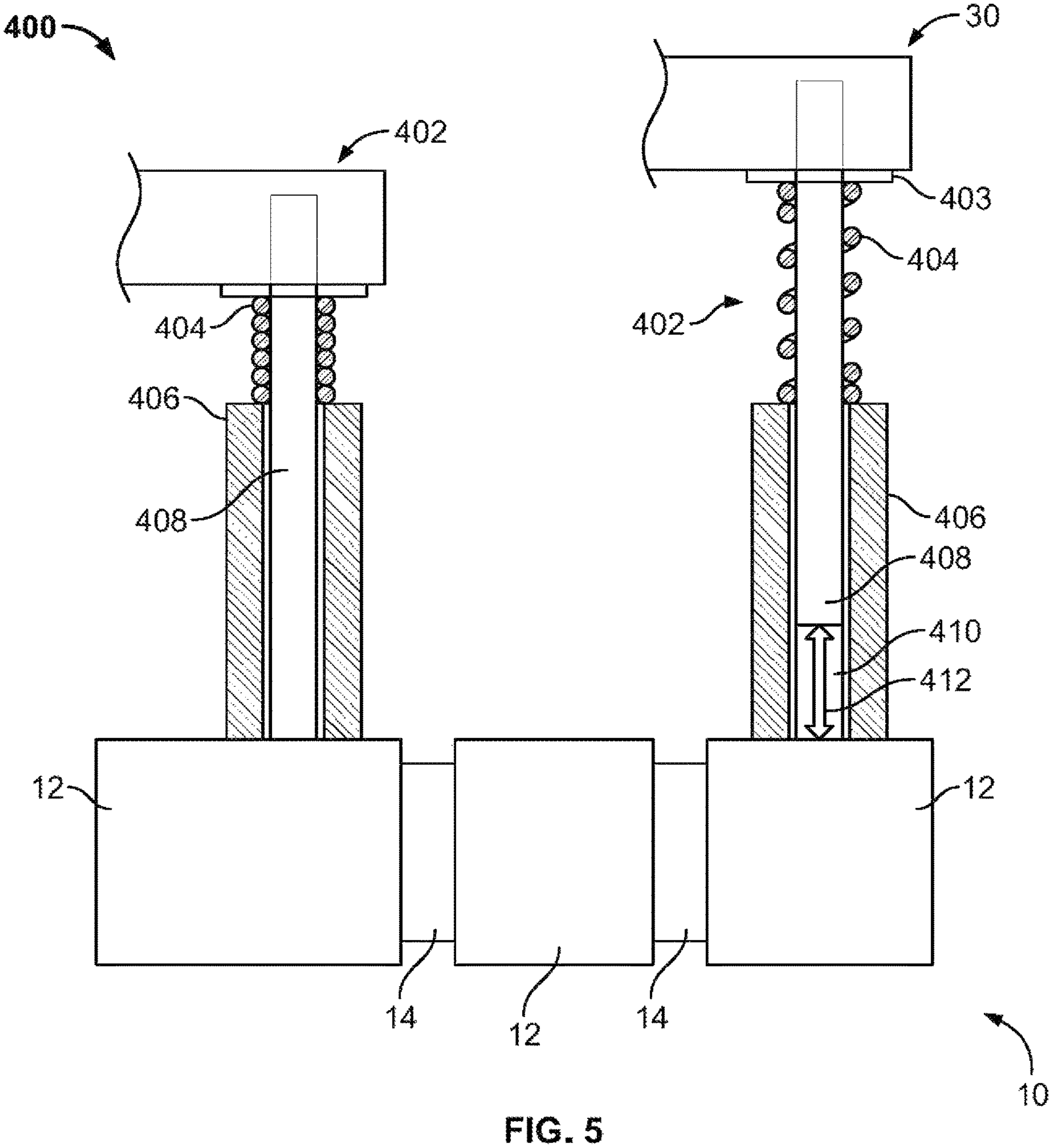
FIG. 5 is a cross-sectional view of an adjustable rod structure according to another embodiment of the present disclosure.

Yet another embodiment adjustable rod is depicted in FIG. 5. In this embodiment, adjustable rod 402 has a spring 404, external sleeve 406, and inner shaft 408. At an end of adjustable rod 402 configured to mate with a retractor assembly is a flange 403. It is noted that any of the foregoing rod embodiments may include a similar flange or like structure. Spring 404 is connected to flange 403 and external sleeve 406 through press-fit, weld, fastener, adhesive, screw, chemical bond, or any other mechanical or chemical securing means. Inner shaft 408 of adjustable rod 402 extends from one end of rod, through flange 403, spring 404 and into external sleeve 406. External sleeve 406 has an internal cavity 412 that extends through a depth of the external sleeve, as shown in FIG. 5. In this way, inner shaft 408 is free to move in an axial direction in response to loads compressing or expanding spring 404. In a variant, the internal cavity 412 may only extend through a portion of the external sleeve length. In either configuration, inner shaft 408 is able to move within the internal cavity 412. As shown in FIG. 5, spring 404 is able to expand in length thereby maintaining a condition where external sleeve 406 remains in contact with vertebral body 12 even when forces are applied to the vertebral body pushing it away from adjustable rod 402.

Figure 6A:
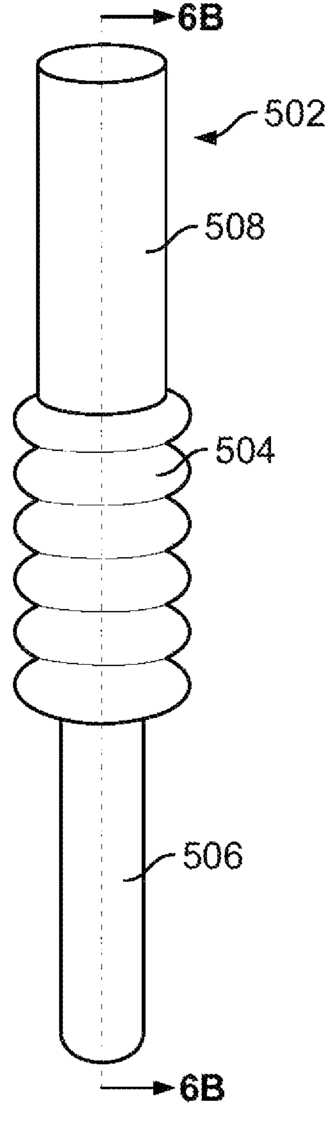
FIG. 6A is a perspective view of an adjustable rod according to another embodiment of the present disclosure.
Figure 6B:
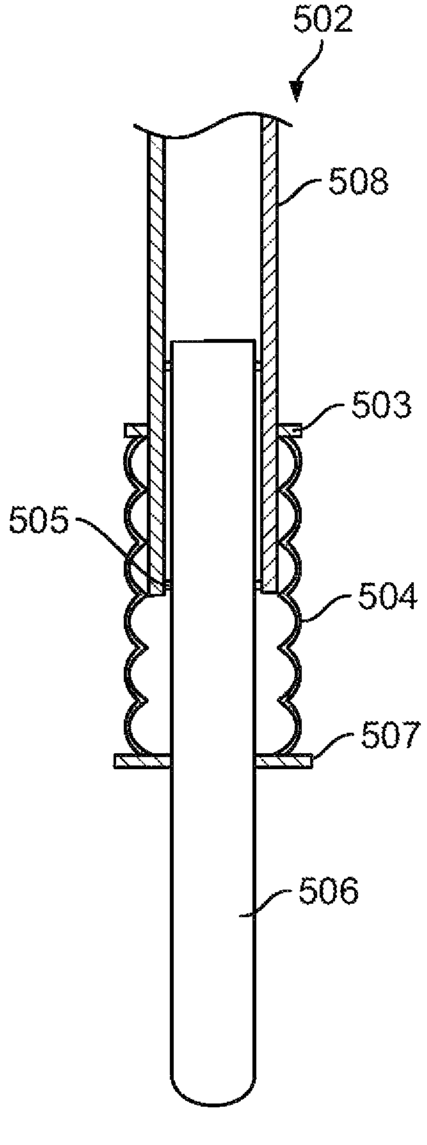
FIG. 6B is a side cross-sectional view of the adjustable rod of FIG. 6A.

In another embodiment shown in FIGS. 6A and 6B, an adjustable rod 502 includes an inner shaft 506, a polymer spring 504 which also functions as a sleeve, and an external shaft 508. External shaft 508 of adjustable rod 502 includes a cavity therein and has an anchor 503 positioned circumferentially and facing outward toward a distal end. Anchor 503 secures to polymer spring 504 as shown in FIG. 6B. Additionally, external shaft 508 includes inward facing anchor protrusions 505 at the distal end of external shaft 508, as best shown in FIG. 6B. Inner shaft 506 is sized to be disposed within external shaft 508 and polymer spring 504 as shown in FIG. 6B and includes an anchor 507 extending circumferentially around inner shaft 506 and configured to secure to one end of polymer spring 504. The upper portion of inner shaft 506 rests inside of the cavity within external shaft 508. In one variant, inner shaft 506 forms a friction interface with the internal walls of external shaft 508 to provide a rod with more controlled expansion and contraction. As indicated above, polymer spring 504 interfaces with anchors 503 and lower anchors 507 and forms an enclosure around a lower portion of external shaft 508 and an upper portion of inner shaft 506. Polymer spring 504 is preferably made out of PEEK or other similar materials. The interfaces among the components of this embodiment may be achieved through friction, press-fit, weld, fasteners, adhesive, screw, chemical bond, or any other mechanical or chemical securing means. Clearance between the distal end of external shaft 508 and anchors 507 on inner shaft is sufficient to allow for an expected range of polymer spring movement.

Figure 7:
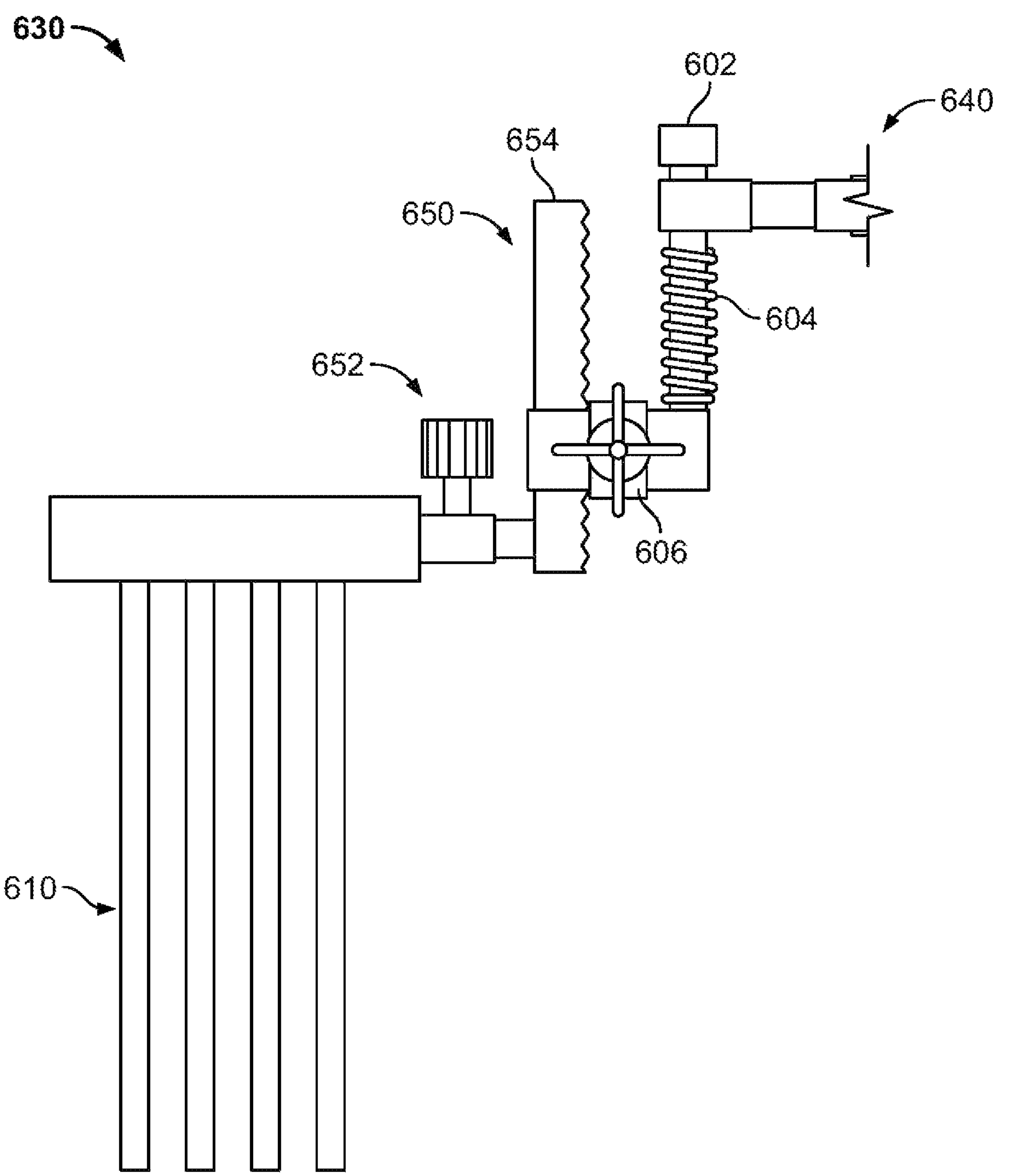
FIG. 7 is a side view of a retractor assembly including a spring component according to one embodiment of the present disclosure.

In other embodiments of the present disclosure, a retractor assembly is itself adjustable. One embodiment of an adjustable retractor assembly is shown in FIG. 7. Retractor assembly 630 includes an adjustable rod structure 610 with a plurality of rods connected to a frame of retractor assembly 630. External securement of the retractor frame is through an adjustment structure 650 including a series of components as shown in FIG. 7. Although the components are shown in a particular configuration in FIG. 7, such configuration is not necessary to realize the advantages of this concept. However, as shown, adjustment structure 650 secures retractor assembly 630 in position through a combination of knobs and screws. An actuating knob 652 secures adjustment structure 650 directly to retractor assembly 630. Actuating knob 606 controls the vertical position of retractor assembly 630 by adjusting the position of vertically adjustable arm 654, which in turn is directly connected to an arm portion extending to actuating knob 652. Remote from retractor assembly 630 and behind actuating knob 606 is spring element 604 extending between actuating knob 606 and arm 640, where arm 640 is secured to a fixed location (not shown). The arm may be an arm as disclosed in the '780 Application.

As depicted, spring element 604 is compressible and expandable in a direction generally parallel to adjustable rod structure 610. Adjustable structure 650 including settings on vertically adjustable arm 654 are modifiable so that upon advancement of the adjustable rod structure into a surgical site, movement of a bone surface near the surgical site will not cause rods to disengage from the bone surface, to the extent such rods are in contact with bone surfaces. In variants, the spring can be located in other positions within an adjustment structure and can be configured to have a maximum range of movement greater or less than that shown in FIG. 7. Materials and configurations for the spring may be substituted with other structures that have elastic properties, such as foam, washers, hydraulic systems, pneumatic systems, or other similar materials. Additionally, the adjustable rod structure and rods making up such structure can be any type of rods contemplated in this disclosure, in the '228 Publication, or those known in the art and any combination of such rods.

Figure 11:
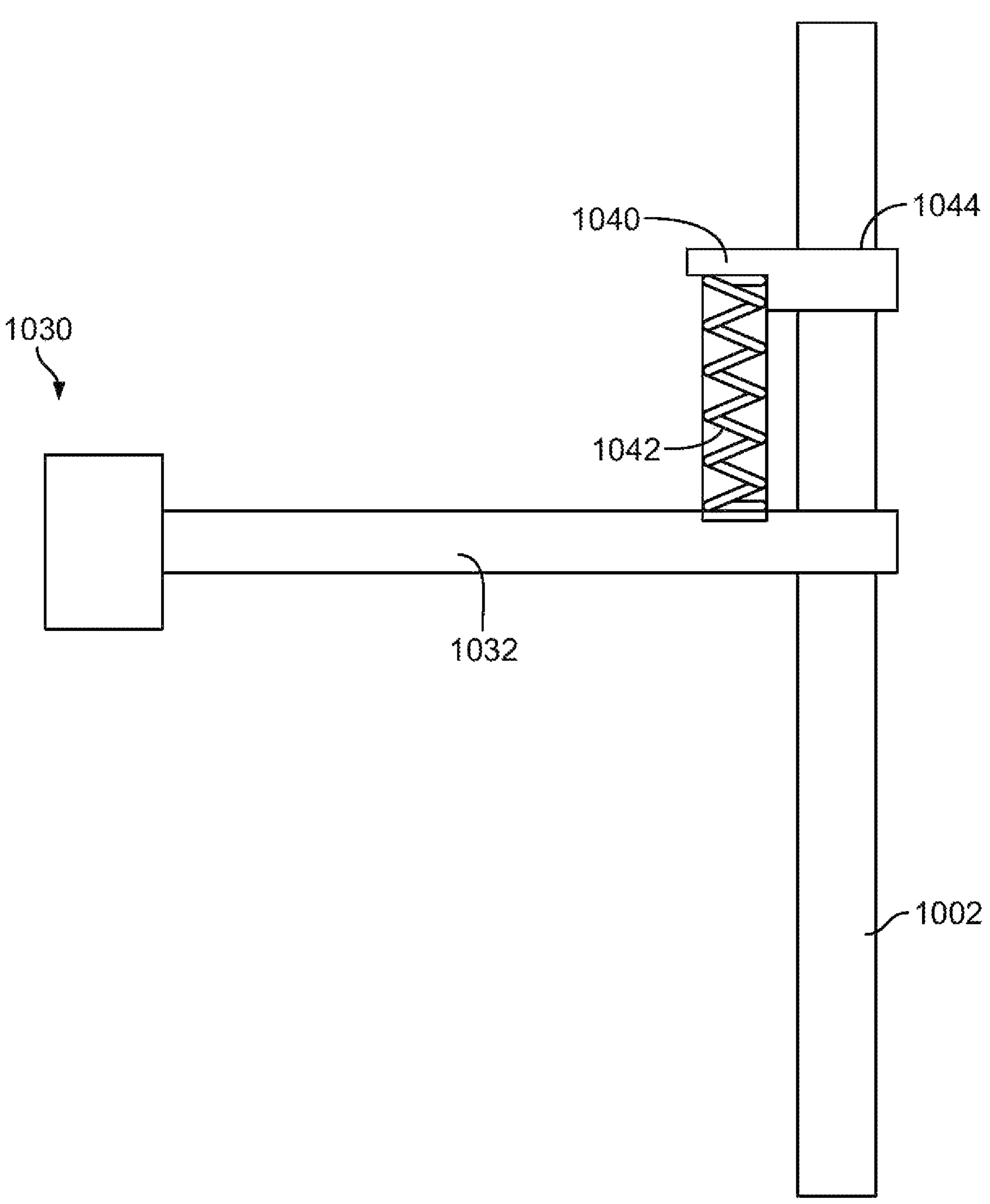
FIG. 11 is a partial sectional view of a retractor having an arm including a spring, according to one embodiment of the present disclosure.

In a manner similar to the immediately preceding embodiment, a spring feature may be incorporated into an arm 1032 of a retractor frame 1030 as shown in FIG. 11, thus removing the need for a spring in the rigid arm or in the rods. As depicted, arm 1032 of the retractor frame includes an attachment 1040 with a spring 1042 disposed therein and an engagement portion 1044 extending orthogonally from the spring. The attachment is structured and positioned on the arm so that the spring is parallel to a rod 1002 when such rod is secured to the attachment. The engagement portion is connected to the spring so that it moves in conjunction with compression or expansion of the spring. In this manner, any load on the frame causing it to move would be absorbed by the spring so that the rod remains stable. This principle could be applied the other way as well, in the event the rod moves due to movement of the patient.

Figure 8:
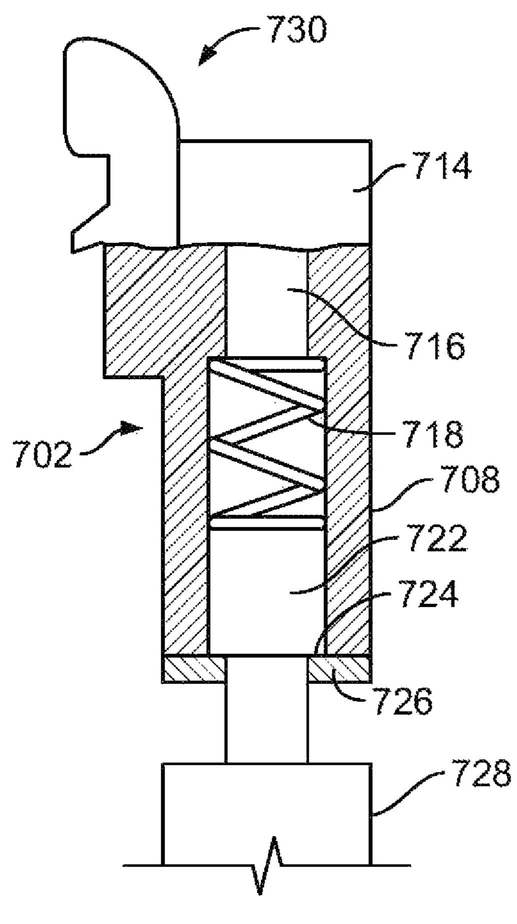
FIG. 8 is a cross-sectional view of an adjustable rod according to another embodiment of the present disclosure.

In yet another embodiment, an adjustable rod 702 includes a spring mechanism at the top of the rod proximal to the connection with a retractor frame 730, as shown in FIG. 8. Adjustable rod 702 includes spring element 718, inner shaft 728 with an upper portion 722, and an outer shaft 708. Upper portion 722 of inner shaft 728 is disposed within a cavity of outer shaft 708. Filing the remainder of the cavity between inner shaft 728 and an upper end of the cavity is spring element 718. That is, spring element 718 is located above inner shaft upper portion 722. The configuration of each element within the cavity is such that spring element 718 is in contact with both outer shaft 708 and inner shaft 728. Outer shaft 708 includes stops 726 as shown in FIG. 8 to limit expansion of spring element 718 and to prevent upper portion 722 from exiting the cavity within outer shaft 708. In a variant, the adjustable rod may operate without the inclusion of stop elements. It is also contemplated that the stop elements may exist within the cavity of the external shaft while still performing the substantially the same function. In yet another variant, the spring may wrap around an upper portion of the inner shaft while still remaining within the cavity of the external shaft.

Figure 9:
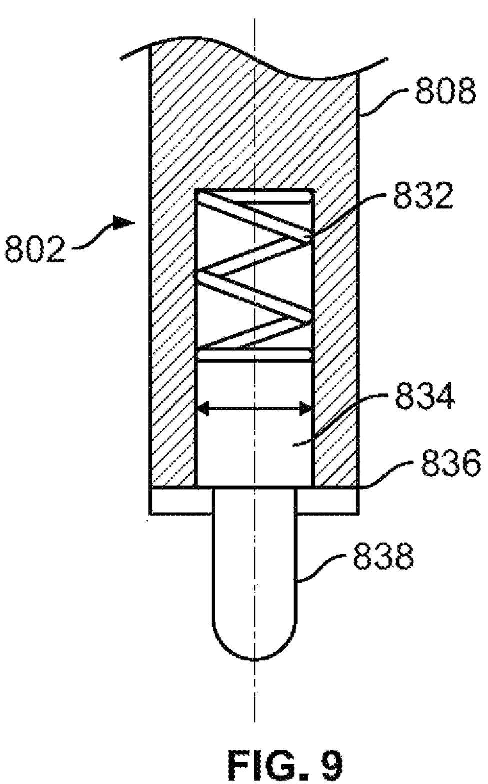
FIG. 9 is a cross-sectional view of an adjustable rod according to another embodiment of the present disclosure.

In another embodiment, a spring element is included in a rod near an end distal to the retractor assembly, as shown in FIG. 9. In this embodiment, adjustable rod structure 802 includes an external shaft 808, spring element 832, inner shaft 834 and a plunger tip 838 extending from inner shaft 834. In an assembled condition and as shown in FIG. 9, a cavity within external shaft 808 houses spring element 832 and inner shaft 834, where the spring is bounded by external shaft 808 and inner shaft 834. As loads bear on adjustable rod structure 802, spring element 832 compresses and plunger tip 838 may retreat into the cavity within external shaft 808. As with the previous embodiment depicted in FIG. 8, external shaft 808 includes stops 836 to prevent inner shaft 834 from exiting the cavity in external shaft 808. Tip 838 is attached to the bottom of inner shaft 834 and may be shaped to have a broad flat surface or a rounded surface. In one example, external shaft 808 has a diameter of 4 mm while a cavity within external shaft has a diameter of 3 mm. In a variant, the spring element can be substituted with a pneumatic element having the same functionality.

In yet another embodiment, an adjustable rod assembly may be provided as depicted in FIGS. 10A-C. Adjustable rod 902 is securable to a retractor assembly 930 generally as shown in the cross-section of FIG. 10A. Adjustable rod 902 includes an upper rod portion 908, a lower rod portion 906, and a wound coil spring 905. In the sectional view shown in FIG. 10B, lower rod portion 906 is visible as disposed within upper rod portion 908. Wound coil spring 905 extends from an end of lower rod portion 906 with additional length coiled outside of adjustable rod 902 on a proximal side when used during surgery. Coil 905 may be any metal suitable for use as a wound material and for "feeding" the coil as shown in FIGS. 10B-C. Adjustable rod 902 is configured so that lower rod portion is extendable in tandem with unwinding of wound coil spring 905. The hollow structure of upper rod portion 908 provides an open space for both wound coil spring 905 and lower rod portion to move therein. Extension of a top end of lower rod portion 906 is limited such that it does not extend outside of the cavity of upper rod portion 908, though in a variant requiring greater maximum length, it need not be so. One advantage of adjustable rod 902 is that its variable length can be used to accommodate a variety of surgical conditions. For example, adjustable rod 902 can be placed to fit into a portal with an 80 mm depth or a portal with a 200 mm depth. Since the adjustable rod covers such a range of lengths, it reduces or even negates the need for multiple rod sizes to accommodate a range of surgical conditions. For example, instead of having a kit with rods ranging in size from 80 mm to 200 mm in length at 10 mm increments, a single adjustable rod 902 may be used.

In another aspect, the adjustable rods can be employed in methods of minimally invasive surgery and in particular to create surgical portals for operating procedures, such as those involving the spine. Although the embodiments herein are described in the context of lateral approaches to the spine, other approaches are also contemplated. These include, for example, anterior and posterior approaches. The choice of approach may depend on the type of implant being placed. For example, an anterior approach may be used for anterior lumbar interbody fusion implants. In addition to procedures involving the spine, the concepts described throughout the specification may also be employed outside of the spine. FIGS. 1A-D depict some of the steps involved in the retraction of adjustable rods 102 to create such a portal. Initially, a guidewire or a similar device is inserted into the patient to identify a path for the insertion and placement of the rods of the adjustable rod structure. Then, a retractor assembly (shown in a later step of the method in FIG. 1A as retractor assembly 30), with adjustable rods attached thereon, is aligned over a target surgical site.

One embodiment of the method of the present disclosure begins with advancement of the rods to the surgical site. Adjustable rod structure 110 is inserted and advanced through tissue of the patient over the guidewire (not shown) until the flat end faces of the rods contact a bone surface, such as a vertebral body 12, as shown. During advancement, adjustable rods 102 extend through the patient's skin 20 and through muscle or any other tissue between skin 20 and the surface of vertebral body 12. Once fully advanced, retractor assembly 30 with adjustable rod structure 110 appears as shown in FIG. 1A. From its fully advanced position, adjustable rod structure 110 is then retracted to displace tissue and increase a size of a portal. In the process of retraction, adjustable rods 102 retract as shown between a closed position shown in FIGS. 1A-B and an open position i.e., retracted, shown in FIGS. 1C-D.

Returning to the initial contact of the rods with a surface, i.e., vertebral body 12, spring portions 104 of rods allow flat end faces 106 to rotate about any axis or combination of axes to best position flat end faces 106 for interfacing with vertebral bodies 12, as shown in FIGS. 1C-1D. Further, the spring portions 104 allow for the lengthening of adjustable rod 102 to accommodate varying depths and shapes of vertebral bodies 12. Thus, the adjustable rods 102 do not need to be adjusted at the retractor 30 in order for flat end faces 106 to properly interface with vertebral bodies 12. The method as depicted in FIGS. 1A-1D illustrates this point. A surface of a vertebral body is curved, and the spring portion of the adjustable rod accommodates for the variable surface of the body by extending and bending about multiple axes, allowing for the flat end face of the adjustable rod to orient in such a way that it forms a uniform interface with the vertebral body.

As noted above, FIGS. 1C and 1D depict the rods as retracted after retraction is performed using a method whereby rods are selectively or as a group retracted in an outward and lateral direction. As shown, the adjustable rods 102 conform to the surfaces of vertebral bodies 12. In particular, spring portion 104 bends in a combination of directions so that flat end faces 106 interface with the vertebral bodies 12. Spring portions 104 operate with a capacity for a wide range of movements allowing flat end faces 106 to rest against vertebral bodies 12 at a multitude of angles and depths while the fixed length portions 108 maintain a secure connection with retractor assembly 30, as noted above. During positioning of the rods proximal to the surgical site and while held in position following retraction, an orientation of fixed length portions 108 remains stable limiting movement due to flexure, while spring portions 104 compress, expand or bend, as described above. In this configuration, the adjustable rods 102 create a stable working space wherein the operator may access, repair, and/or replace an intervertebral disc 14, for example. In addition, once the spring portions 104 of each adjustable rod 102 contact vertebral bodies 12, any downward movement or load bearing on retractor assembly 30 or upward movement due to displacement of the spine is absorbed at least in part and typically fully by the springs. In this way, adjustable rods 102 automatically respond to spine and other movements to protect the vertebral surfaces from potentially damaging impacts. At the same time, the stability provided by the adjustable structure of adjustable rods 102 ensures that a portal path is maintained and that the rods do not recede or otherwise withdraw from the surgical site, thus avoiding circumstances where the portal could be exposed to tissue creep or other unwanted effects. Due to the secure interface between flat end faces 106 and vertebral bodies 12, a stable operating void is created that allows the operator to access intervertebral disc 14 for repair, replacement, fusion, or other surgical procedures.

With rods in position and a portal to the surgical site created, additional steps may then be performed to ensure the portal remains open during surgery. Such approaches are outlined in the '228 Publication, for example.

All embodiments of the present disclosure operate to achieve a similar objective. In another embodiment, adjustable rod 202 is employed in a method of creating and maintaining a surgical portal in a patient. The steps of using one or more adjustable rods 202 are largely similar to that described for adjustable rod 102, although certain nuances are mentioned here for clarity. When adjustable rod 202 makes contact with a surface, such as a surface of a vertebral body, external shaft 208 moves downward 220 toward internal shaft 206 and spring element 204 compresses in unison with the downward movement of external shaft 208. Loads bearing on adjustable rod 202 are absorbed by spring portion 204, reducing or eliminating any loads transferring through adjustable rod 202 to the surface below the rod. In the fully extended or withdrawn position of adjustable rod 202, mechanical stop element 214 is at the bottom of slot 212. In this manner, as external shaft 208 moves downward slot 212 slides over mechanical stop. Although spring element 204 expands and compresses 220 in response to changes in loading, compression is limited to the extent mechanical stop encounters a proximal end of slot 212.

In one embodiment, adjustable rod 302 appears as shown in FIG. 4. When subject to loading, such as when rod 302 contacts a bone surface spring portion 304 compresses and upper portion 308 moves closer to lower portion 306. As this occurs, inner portion 305 slides further into cavity 310. Overall, a length of adjustable rod 302 decreases when a load is applied as the spring portion is compressed. Bending of spring portion 304 may be limited to the extent its movement is bound by walls of cavity 310. The elements move in the reverse direction when the load is withdrawn. Other aspects of the method are as described for rod 102 above.

The embodiment 400 of FIG. 5 operates in a similar manner as that of the embodiment of FIG. 4. An inner shaft 408 of adjustable rod 402 slides downward into external sleeve 406 when adjustable rod 402 is subject to load, spring 404 compressing over inner shaft 408 during this process. In a fully contracted state, inner shaft 408 extends to the bottom of external sleeve 406 and may rest against vertebral body 12. When spring 204 expands, i.e., when loads are released or when the retractor pulls away from the rods, external sleeve 406 translates in an axial direction in response to the expansion of the spring, thus creating a longer overall rod.

The embodiment 500 of FIGS. 6A-B employs a polymer spring 504 positioned between an upper anchor 503 and lower anchor 507 so that rod 502 is compressible and expandable. When adjustable rod 502 is under load, e.g., compression from pressure on a surface below the rod, inner shaft 506 is in contact with a vertebral body 12, causing polymer spring 504 to compress as inner shaft 506 slides into the internal cavity of external shaft 508. A maximum deflection in polymer spring 504 is limited by the placement of upper anchor 503 and lower anchor 507.

The adjustment structure shown in FIG. 7 operates to stabilize retractor assembly 630 and rods during various aspects of surgery. For example, when a surgeon is applying load onto a bone near the surgical site, such as via a mallet. In another example, the patient may physically shift his or her position. Assembly and securement of adjustment structure 650 shown in FIG. 7 is accomplished using methods as known by those of ordinary skill in the art. As part of this process, it is important that the arm 640 of the adjustment structure be secured to a fixed location in order to ensure stability of each component. Once adjustment structure 650 is roughly positioned, knobs 606, 652 and other adjustment mechanisms are used to refine the position of the retractor assembly 630. In addition, knob 606 may be used to adjust a vertical position of retractor assembly 630. During surgery, it is often necessary for the operator to apply considerable force to the patient's body, which may cause the patient's body to move or shift. A typical retractor setup is rigid and cannot accommodate for this movement, which may cause misalignment between the rods of the retractor assembly and the vertebral bodies of the patient. Adjustment structure 650 is advantageous in that it addresses these concerns through the inclusion of spring element 604. When the patient's body moves during surgery, spring element 604 will compress or expand, thus allowing rods 610 to remain stable relative to the patient's body. It is understood that methods employing the retractor assembly 630 and associated adjustment structure 650 may include adjustable rod structures 610 that include any one or more of the adjustable rods described in the various embodiments herein. Additionally, any combination of such rods may also form part of the adjustable rod structure. Operation of retractor 1030 with an arm 1032 having a spring 1042, see FIG. 11, is similar to that described for the adjustment structure of FIG. 7. To secure a rod 1002 to arm 1032, rod 1002 is secured to extension 1044 and may pass through or engage with arm 1032 as well.

In still further embodiments, the rods shown in FIGS. 8 and 9 are employed in methods of forming a surgical portal in a patient. Compression and expansion of these rods is similar to that described for rod 302 shown in FIG. 3.

Another alternative embodiment of a method to maintain a consistent interface with the vertebral bodies is shown in FIGS. 10A-C, where the interface between lower rod portion 906 and a vertebral body is maintained through unwinding wound coil spring 905 and securing it in position. Once the adjustable rod 902 is inserted past patient's skin 20, the rod 902 is not immediately interfacing with a vertebral body without further advancement, as is shown in FIG. 10B. To extend rod 902 to the intended surface for placement, would coil spring is uncoiled, or pushed, causing a lower end of coil 905 to push lower rod portion 906 further into the body of the patient. This pushing of coil 905 continues until lower rod portion 906 reaches a target depth, typically near or against a surface such as that of a vertebral body, as is shown in FIG. 10C. In this configuration, upper rod portion 908 may be locked relative to lower rod portion 906 to maintain the extended length of rod 902, or coil 905 can be secured to upper rod portion 908, for example.

In any of the above methods, the adjustable rod structure can include a probe therein during initial insertion into the body of the patient, i.e., in between the rods, such as those described in the '228 Publication. When advancing the rod structure with the probe, the rods may be positioned proximally relative to a distal tip of the body of the probe. In this manner, only the probe will initially advance through the tissue, and once partially advanced, the rods on the probe will enter the body. When the probe reaches the surgical site, the rods will keep advancing until they also reach the surgical site. This variation of the method can be advantageous where a more gradual distraction of the surgical portal is desired.

In any of the above embodiments, a depth of one or more of the rods of an adjustable rod structure may be independently adjusted at any step during the creation of the surgical portal. For example, once the adjustable rod structure is fully inserted to a desired location in the body of the patient, one rod of five can be raised or lowered to fine tune the rod position for better positioning to retract the rods. When it is an adjustable rod that is withdrawn, securement to a bone surface near the surgical site can be maintained due to the expansion of the spring component on the rod.

Variations

Each adjustable rod or retractor described above may vary in shape as a matter of design choice. Rods may have circular, rectangular, polygonal, oblong, D-shaped, oval, and many other cross-sectional shapes as a matter of design choice and surgical application. Additionally, a length of each rod or the length between different rods of a retractor may vary to suit design needs for each of the contemplated embodiments. Materials as described for certain embodiments may also be used in others as a matter of design choice. It is also contemplated that features of the rods described for certain embodiments may also be incorporated into other embodiments.

Lateral Access Alignment Guide and Rigid Arm

The structures, systems and methods as described herein may be used in surgical settings where a retractor holding rods intended for expansion is supported by the rigid arm or frame of the '780 Application. Additionally, alignment to determine an insertion location for inserting the same rods into the body may be performed using an alignment guide described in the '780 Application.

Lateral Access Bridges, Shims and Lighting Including Rod Lighting

The structures, systems and methods as described herein may be part of a surgical procedure where after the surgical portal is fully expanded, bridges designed to maintain the portal size and shape and to provide light to the portal may be inserted to improve and enhance the surgical procedure, such as those described in the '796 and '579 Applications. Rods, shims and other retractor components may also be used as described in the '579 Application.

Expanders for Rod Retraction

The structures, systems and methods as described herein may be part of a surgical procedure where at least some of the steps involved in distracting rods of a retractor involve the insertion of expanders in between the rods as described in the '847 Application, thereby increasing a surgical portal size in between such rods.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A retractor assembly comprising:

a retractor adjustment apparatus configured for releasable attachment to a base structure, the retractor adjustment apparatus including a first portion with a spring aligned along an axis and a second portion extending from the first portion in a direction transverse to the first portion; and a retractor frame attached to an end of the second portion of the retractor adjustment apparatus that is spaced apart from the axis, the second portion separating the retractor frame and the first portion of the retractor adjustment apparatus, the retractor frame including a plurality of tissue retraction members attached thereto, wherein the retractor assembly is configured such that when a free end of one of the tissue retraction members is pressed against a surface, the retractor frame moves relative to a portion of the retractor adjustment apparatus.

2. The retractor assembly of claim 1, wherein the retractor adjustment apparatus further comprises:

an extension support portion attached to the spring and the retractor frame, wherein the extension portion includes a first support arm and a second support arm movable relative to the first support arm.

3. The retractor assembly of claim 2, wherein the first support arm is an interconnecting block attached to the spring and the second support arm is an adjustable arm movably attached to the interconnecting block and holding the retractor frame, the adjustable arm being axially translatable relative to the interconnecting block in response to actuation of a knob operatively connected to the interconnecting block.

4. The retractor assembly of claim 3, wherein the retractor adjustment apparatus further comprises a retractor extension arm attached to the adjustable arm and the retractor frame, the retractor extension arm including a second knob disposed thereon, the second knob being actuatable to control a distance between the spring and the retractor frame, and the knob being a first knob.

5. The retractor assembly of claim 4, wherein the first and second knobs are configured such that actuation of the first knob causes the retractor frame to move in a first direction relative to the base structure and actuation of the second knob causes the retractor frame to move in a second direction relative to the base structure, the second direction being at an angle relative to the first direction.

6. The retractor assembly of claim 2, wherein one of the first support arm and the second support arm is a retractor extension arm directly attached to the retractor frame and including a knob, the knob being actuatable to control a distance between the spring and the retractor frame.

7. The retractor assembly of claim 1, wherein the retractor assembly is configured such that when the free end of the one of the tissue retraction members is pressed against a surface, the retractor frame moves closer to a plane perpendicular to a first central longitudinal axis of the one of the tissue retraction members, the plane passing through a location on the retractor adjustment apparatus configured for attachment to the base structure.

8. The retractor assembly of claim 1, wherein the plurality of tissue retraction members include either a plurality of blades or a plurality of rods.

9. The retractor assembly of claim 1, further comprising the base structure attached to the spring and a fixed location, the base structure being an arm or a rail.

10. An intermediate support frame for use with a surgical access instrument comprising:

a resilient member configured to attach to a base structure;

an interconnecting block attached to the resilient member; and an adjustable arm operatively connected to the interconnecting block, the adjustable arm configured to hold a surgical access instrument, wherein the adjustable arm is configured to be actively manipulated to translate the adjustable arm with respect to the interconnecting block, and wherein when the intermediate support frame is attached to the base structure and the surgical access instrument, forces applied onto the surgical access instrument or the base structure are at least partially absorbed by the resilient member as the surgical access instrument and the base structure move with respect to each other.

11. The intermediate support frame of claim 10, wherein the adjustable arm is configured to hold a surgical access instrument in the form of a retractor with a plurality of tissue retraction members such that when the adjustable arm is attached to the retractor and the plurality of tissue retraction members are pressed against a surface, the retractor moves parallel to an axis of the resilient member and toward or away from a plane perpendicular to the axis.

12. The intermediate support frame of claim 10, wherein the adjustable arm is configured to be linearly translatable with respect to the interconnecting block in response to actuation of a rotatable control member disposed on the interconnecting block.

13. The intermediate support frame of claim 12, wherein the adjustable arm is configured to be adjustable in predetermined increments with respect to the interconnecting block in response to actuation of the rotatable control member.

14. The intermediate support frame of claim 10, wherein the adjustable arm further comprises an extension member configured to be directly attached to the surgical access instrument, the extension arm including a rotatable control member actuatable to change a distance between the surgical access instrument and the adjustable arm.

15. The intermediate support frame of claim 14, wherein a direction of movement caused by actuation of the rotatable control member is perpendicular to a direction of movement of the adjustable arm relative to the interconnecting block.

16. The intermediate support frame of claim 10, wherein an elongate dimension of the resilient member is parallel to an elongate dimension of the adjustable arm.

17. The intermediate support frame of claim 10, wherein the resilient member is a spring.

18. A method of using a retractor assembly comprising:

compressing a spring member of a first portion of a retractor adjustment apparatus in response to a force being applied to a base structure holding the retractor adjustment apparatus or to a retractor supported by a second portion of the retractor adjustment apparatus, wherein compression of the spring member brings the retractor closer to a plane through the base structure, the plane being perpendicular to a central longitudinal axis through the spring member, and wherein the retractor is entirely spaced apart from the central longitudinal axis.

19. The method of claim 18, further comprising rotating a rotatable control on a connection block of the retractor adjustment apparatus to change a position of an adjustable arm holding the retractor relative to the spring member.

20. The method of claim 19, further comprising rotating a rotatable control on an extension member of the retractor adjustment apparatus to change a distance between the adjustable arm and the retractor, the extension member extending between the adjustable arm and the retractor.

* * * * *